United States Patent [19]
Shemoney

[11] Patent Number: 6,101,874
[45] Date of Patent: Aug. 15, 2000

[54] MEASURING THE GOLD RATIO OF CAST GOLD

[76] Inventor: Yossi Shemoney, Mobile Post Misgav 20182, Jerusalem, Israel

[21] Appl. No.: 09/077,235
[22] PCT Filed: Nov. 21, 1996
[86] PCT No.: PCT/IT96/00159
  § 371 Date: Aug. 12, 1998
  § 102(e) Date: Aug. 12, 1998
[87] PCT Pub. No.: WO97/20208
  PCT Pub. Date: Jun. 5, 1997

[30] Foreign Application Priority Data

Nov. 26, 1995 [IL] Israel ......................................... 116138

[51] Int. Cl.$^7$ ..................................................... G01N 9/08
[52] U.S. Cl. .................................................................. 73/437
[58] Field of Search ................................... 73/32 R, 866, 73/437

[56] References Cited

U.S. PATENT DOCUMENTS

| 2,650,494 | 9/1953 | Linhurst | 73/437 |
| 3,246,504 | 4/1966 | Holff et al. | 73/32 R |
| 3,885,639 | 5/1975 | McLerrin | 177/172 |
| 4,210,027 | 7/1980 | Patterson | 73/866 |
| 4,262,201 | 4/1981 | Wallisch | 378/54 |
| 4,372,405 | 2/1983 | Stuart | 73/437 |

*Primary Examiner*—Thomas P. Noland
*Attorney, Agent, or Firm*—Mayer, Brown & Platt

[57] ABSTRACT

The present invention relates to a non-destructive method for measuring the ratio of gold in carats or the ratio of other components in a cast material. The invention also relates to a method for measuring a specific weight of a cast body including a repeated flooding of the body in a tank with baskets and liquid.

5 Claims, 2 Drawing Sheets

MEASURING THE GOLD RATIO OF CAST GOLD

BACKGROUND OF THE INVENTION

1. Field of the Invention

The present invention generally relates to the accurate measurement, without destruction, of metal components. More specifically, the present invention relates to a method for measuring the ratio of gold in cast cold, or the ratio of other components in a cast material.

2. Description of the Related Art

The gold ratio in cast gold is measured in "carats." The carat is the proportionate weight of one twenty-fourth of the weight of the given body, such as tie ratio of pure gold compared with the alloys. Pure gold has a ratio of 24 carats, that is to say, one hundred percent gold. Workshops and producers of jewelry perform the casting of gold with various alloys. The casting is performed in permanent ratios of alloy to gold and in different types of alloys. "Types" of gold are separated from each other in accordance with the type and/or quantity of alloys in the cast. Casting always causes a change in the ratio of gold found in the cast. Therefore it is necessary to measure the ratio of gold in the cast performed, in carats. The performer of the cast requests to measure the ratio of gold that will be received after the casting.

Today, the known way in which the manufacturers of jewelry measure the ratio of gold in cast gold in the jewelry they produce, is to take a sample of each cast they performed in the workshop to an assayer, who performs a test of the ratio of gold in the sample in order to break down and separate the various components of the sample for the purpose of calculating the ratio of gold within it. This process is expensive, troublesome, long and cannot always be performed in-house. The present invention makes an immediate test possible, at the location of the production.

SUMMARY OF THE INVENTION

The present invention is a method for measuring, without destruction, of the ratio of gold in cast gold or of the ratio of material in the cast in another cast, and a device which performs the measurement using this method.

One of the stages in the method according to the present invention is, the measurement of the specific weight of the cast through the method of submersion in liquid, however, in a special way. In the accepted manner of this method, the body being measured is first weighed in the air and afterwards weighed submerged in liquid when the specific weight of the liquid is known. From the difference between the weights, the specific weight is calculated, which is: body weight divided by the decrease of body weight after submersion in liquid multiplied by the specific weight of the liquid.

Since the bodies referred to herein are primarily very small, principally jewelry, inaccuracies in measurement are caused by problems of surface tension between the liquid and the body and in principal by the creation of air bubbles attached to the measured body at the time it is submerged in liquid. The present invention method is the "Repeated Flooding" method is used—for improving the accuracy of measuring the specific weight of the cast body. For the purpose of deduction the air bubbles and the good joining between the liquid and the body, the body is not merely submerged in the liquid. Rather, the body is placed in a tank and flooded with liquid. Afterwards, the tank is emptied and flooded again. After a number of repetitions of this process, the measured body remains submerged in the liquid without air bubbles and without the spaces created by problems of surface tension. That is to say, "Repeated Flooding," instead of mere submersion. The mathematical equation is identical in the two methods.

BRIEF DESCRIPTION OF THE DRAWINGS

The invention is described by FIGS. 1 and 2. These figures do not intend in any way to limit the scope of the invention and are intend solely for clarifying description.

DETAILED DESCRIPTION OF THE INVENTION

Figure 1:
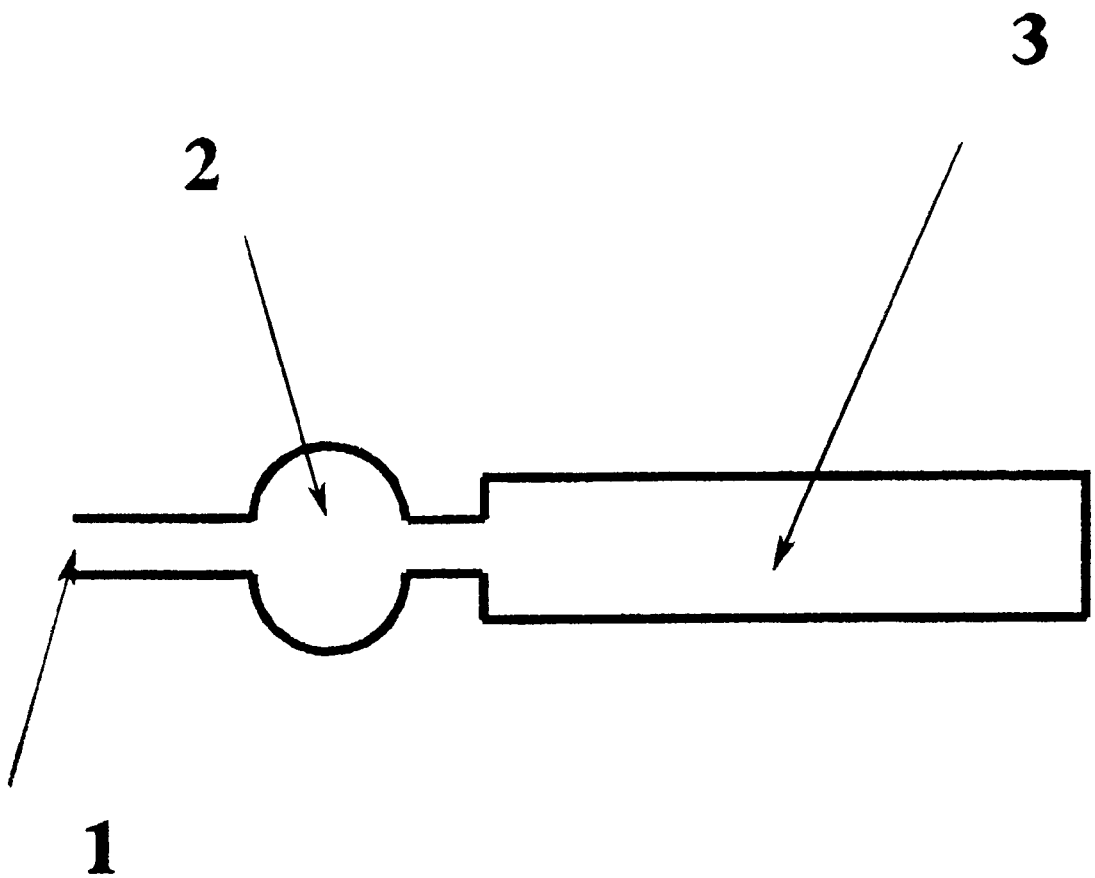
FIG. 1 describes an example structure of cast gold with porosity traps which is used in the method.

The method for measuring the ratio level of gold in cast gold or the ratio of cast material of a body from another cast, according to the present invention, is comprised from the following steps, when the steps "A" through "D" are performed in a one-time manner for each type of gold and the steps "E," and "F" are performed for each test of new tested body;

a. Casting "standard" reference samples, for every type of gold, according to the following steps:
   a1. Building a cast structure with or without a porosity trap, a stricture for centrifugal casting as described in FIG. 1, including entry pipe (1), a space for trapping porosity (2) and a cylinder space (3) to be filled with material of the cast;
   a2. Casting gold within the cast structure and within the cylinder space of the structure (3) and the cylinder receives the cast gold;
   a3. The cylinder presents a "standard" for measurement;
b. Measurement of the ratio data in carat, of the standard, according to the following steps:
   b1. Testing a portion of the same cast by assaying method, well known as the standard gold testing method;
   b2. Ratio data of the standard is received, this data is the gold ratio of the standard in carats—CT,
c. Measurement of the specific weight of the standard by the following steps:
   c1. First weighing of the standard when it is in the air;
   c2. Second weighing of the standard when it is submerged in liquid, using the "Repeated Flooding" method;
   c3. Calculating the specific weight of the standard by means of the formula $$D_m = \frac{A * D_0}{P}$$

when $D_m$—is the specific weight requested of the standard, $D_o$—is the specific weight of the liquid, in accordance with its temperature during the test, which floods the standard, A—is the we ight of the measured body (the standard) in air, P—is the difference between the first weighing in the air and the second in liquid;
d. Calculating the specific weights of the alloy in the standard using either alloy specification or according to the formula $$L = \frac{A_u * D_m * (1 - CT_m)}{A_u - CT_m * D_m}$$

when L—is the specific weights of the alloy, $A_u$—is the specific weight of pure gold, $D_m$—is the specific weight of the "standard," $CT_m$—is the gold ratio in the standard in carats as determined by the assayer's test;

e. Measurement of the specific weight of the measured body, the body whose gold ratio is requested for measurement, in the same manner through which the specific weight of the standard is measured;

f. Calculation of the gold ratio of the measured body by using data from the standard from the same type of gold and the formula $$CT_s = \frac{A_u * (1 - L/D_s)}{A_u - L}$$

when $CT_s$—is the gold ratio of the measured body in carats, $A_u$—is the specific weight of pure gold, L—is the specific weight of alloy in the standard from the same type of gold as the measured body and $D_s$—is the specific weight of the measured body.

The cast, made out of the spherical space (no.2 FIG. 1), is used for measuring the porosity by the same method in the present invention.

The present invention also includes a device which measures the gold ratio of cast gold in a body cast by means of the method for measurement in the present invention.

The device for measuring the gold ratio of cast gold is comprised of a scale, a hanger for weighing, to which to a small basket is attached by means of strings, an upper tank, a lower tank, a pump, surfactant and software.

Figure 2:
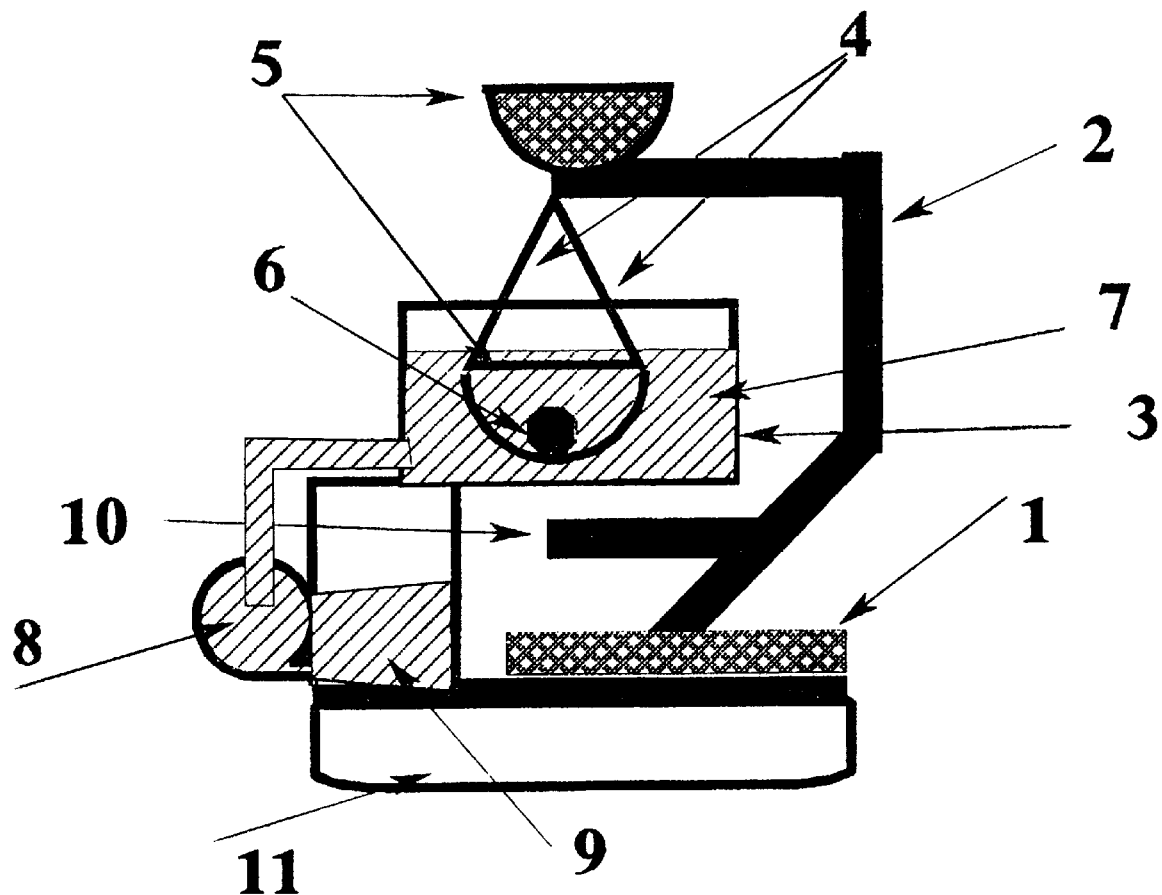
FIG. 2 describes the device for measuring the ratio of gold using the method of the present invention.

FIG. 2 describes the device which includes microprocessor which remembers the various measured data and which uses every measurement in coordination with the appropriate "istandard" and performs the calculations according to the method heretofore described herein, the device also includes a scale (1) for performing the weighing and on it is installed a hanger (2) upon which is connected, by means of strings (4), two small baskets (5), within which rests the tested body (6). The tipper small basket is for the first weight done in the air. The lower small basket, together with the measured body are submerged in to the upper tank (3), and in this situation the first weighing is performed. The pump (8) floods the measured body in liquid (7) which is moved from the lower tank (9) to the upper tank (3). The pump empties the upper tank and floods again a number of times and only afterwards is the second weighing performed. The micro-controller with software, keyboard and display (11) by means of the formulas and by calculation of the ratio of the appropriate standard and weight data of the measured body, calculates in carats the ratio of gold in the measured body and presents it on the display together with the deviation from the gold ratio of the standard. In the event weights are required for balancing the hook (2), the hanger includes a place for adding balancing weights (10).

The method and the device in the present invention perform measurement of the level of the gold ratio of cast gold or of another cast body, without destruction and in a more accurate manner.

I claim:

1. A non destructive method for measuring the ratio of gold in carats or the ratio of other components in a cast material having the following steps:

a. casting of "standard" reference samples, for each type of gold, comprising:
      a1. building a casting structure with or without a porosity trap;
      a2. casting gold from tile type specified within the structure and the casting presents a standard;
   b. measuring the ratio data in carat, of the standard, comprising:
      b1. testing a portion of the said casting of the standard by the standard gold testing method;
      b2. receiving the ratio data of the standard tested and this data is the gold ratio of the standard in carats—CT;
   c. measuring of the specific weight of the standard comprising:
      c1. weighing of the standard when it is in the air;
      c2. weighing of the standard by second weighing when it is submerged in liquid, by the method of "Repeated Flooding";
      c3. calculation of the specific weight of the standard;
   d. calculating the specific weights of the alloy in the standard using either alloy specification or according to the formula $$L = \frac{A_u * D_m * (1 - CT_m)}{A_u - CT_m * D_m}$$

when L—is the specific weight of the alloy, $A_u$—is the specific weight of pure gold, $D_m$—is the specific weight of the standard, $CT_m$—is the gold ratio of the standard in carats;

e. measuring the specific weight of the measured body by way of the specific weight of the standard; and
   f. calculating the gold ratio in the measured body by means of the standard data from the same type of gold as the measured body and the formula $$CT_s = \frac{A_u * (1 - L/D_s)}{A_u - L}$$

when $CT_s$—is the gold ratio of the measured body in carats, $A_u$—is the specific weight of pure gold, L—is the specific weight of the alloy in the standard from the same type of gold as the measured body and $D_s$—is the specific weight of the measured body.

2. A device, for a non destructive measurement of the gold ratio of cast gold or of the material ratio of a body cast using the method claimed in claim 1, comprising a microprocessor for calculating and memory, a first means for weighing the measured body cast in the air, a second means for weighing the measured body cast in liquid, surfactant liquid and a pump which floods repeatedly the measured body with liquid having from the lower tank.

3. A device, for a non destructive measurement of the gold ratio of cast gold or of the material ratio of a body cast as claimed in claim 2 wherein a scale for the weighing of the measured body and a hanger to which a small basket is attached by strings, within which rests the measured body.

4. A method for measuring a specific weight of a cast body comprising:

a. weighing the measured body in the air, hanging within tile tank;
   b. flooding the body in surfactant so that its specific weight is known, by filling the tank;
   c. taking out the liquid from the tank and repeating the flooding, a number of times;

d. weighing the measured body when it is flooded in liquid; and e. calculating the specific weight of the body according to the formula $$D_m = \frac{A * D_0}{P}$$

when D—is the specific weight requested, $D_0$—is the specific weight of the liquid which floods the standard, A—is the weight of the measured body in the air, and P—is the difference between the first weighing in the air and the second in liquid.

5. A non destructive method for measuring the ratio of gold in carats or the ratio of other components in a cast material as claimed in claim 1 wherein the casting structure described in step a1 is without a porosity trap.

* * * * *